United States Patent [19]

Bauer

[11] Patent Number: 4,603,113
[45] Date of Patent: Jul. 29, 1986

[54] CORROSION TESTING

[76] Inventor: Donald Bauer, 551 Walsh Dr., Casper, Wyo. 82601

[21] Appl. No.: 588,515

[22] Filed: Mar. 12, 1984

[51] Int. Cl.$^4$ .................. G01N 31/00; G01N 17/00
[52] U.S. Cl. .................................. 436/6; 73/61.2; 73/86; 422/53; 166/902
[58] Field of Search .............. 73/61.2, 86; 422/53; 436/6; 166/244 C; 175/40

[56] References Cited

U.S. PATENT DOCUMENTS

| | | | |
|---|---|---|---|
| 2,994,778 | 8/1961 | Marsh | 73/86 |
| 3,124,771 | 3/1964 | Rohrback | 422/53 |
| 3,718,034 | 2/1973 | Swearingen | 73/86 |
| 4,142,402 | 3/1979 | Mattioli et al. | 422/53 |

Primary Examiner—David L. Lacey
Attorney, Agent, or Firm—Dean P. Edmundson

[57] ABSTRACT

Techniques and apparatus are described for measurement of corrosion of drill pipe in a well bore during drilling. The techniques involve the use of a test coupon attached to the external surface of a drill string. In a preferred embodiment the test coupon comprises a metal plate mounted in an insulating material such as plastic. The test coupon is preferably secured within a recess in the external surface of a sub connected between segments of a drill string.

10 Claims, 5 Drawing Figures

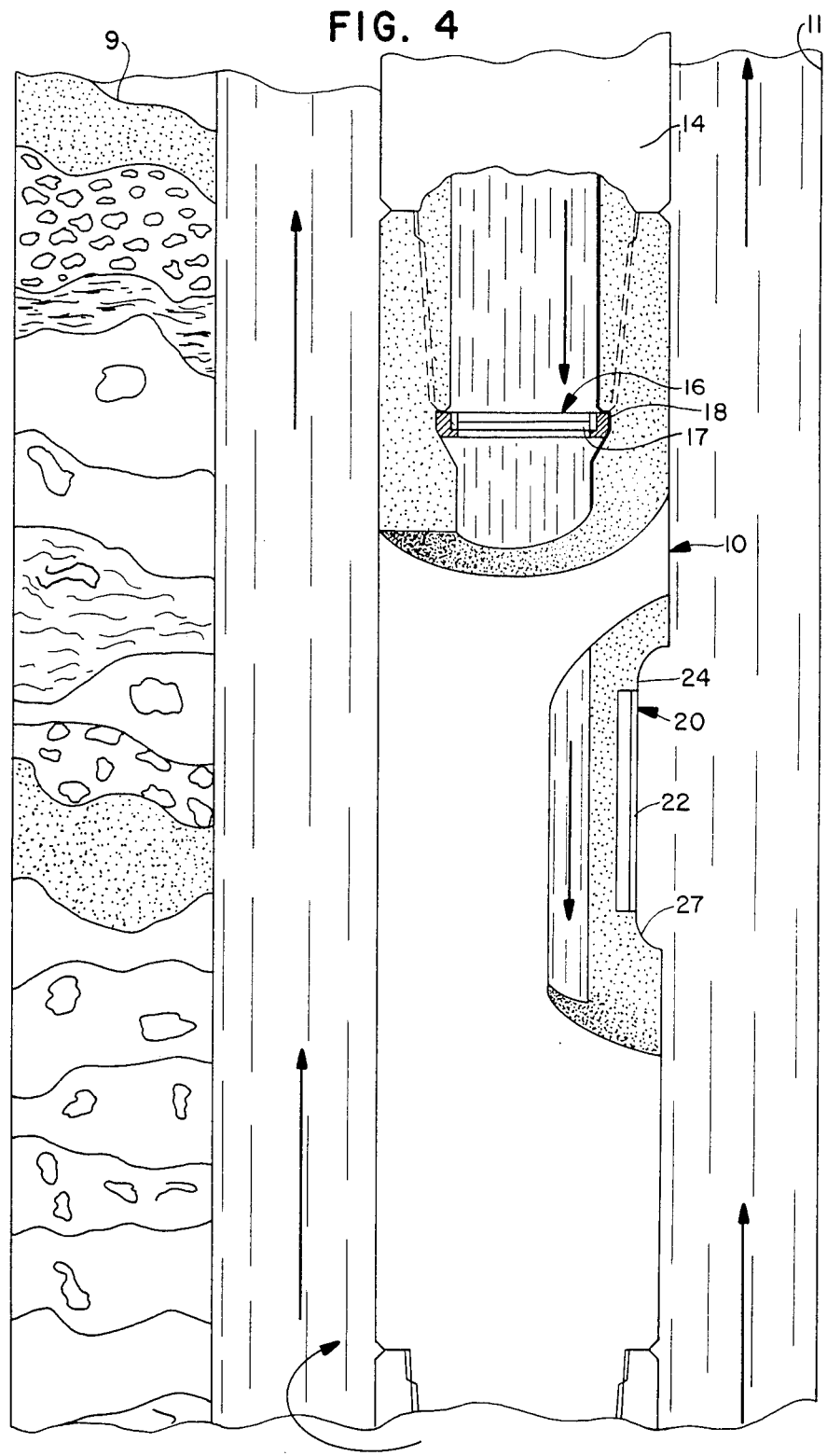

CORROSION TESTING

FIELD OF THE INVENTION

This invention relates to corrosion testing. More particularly, this invention relates to corrosion testing of a drill string in a well bore.

BACKGROUND OF THE INVENTION

In the drilling and servicing of wells (e.g., oil and gas wells) the pipe and other equipment which must be placed into the well bore are necessarily subjected to many corrosive fluids of various types which can be quite harmful to the pipe and equipment. Although it has been previously known to place a corrosion test ring inside the pipe string to measure corrosion effects in the interior of the pipe, there has not previously been described any system for measuring corrosion effects on the exterior of the pipe, nor has there been suggested any desirability for attempting to measure such corrosion.

SUMMARY OF THE INVENTION

In accordance with the present invention there are provided techniques and apparatus for measurement of corrosion of a drill string in a well bore during drilling and the like. The techniques involve the use of a test coupon attached to the external surface of the pipe, or to a sub contained in the drill string.

In one embodiment there is provided an annular corrosion sub which comprises a cylindrical body with a longitudinal bore therethrough. The sub is adapted to be connected between adjacent segments of the drill string. A test coupon is attached to the external surface of the sub and is adapted to be exposed to fluids in the well bore externally of the sub.

The test coupon of the invention, in one embodiment, comprises a metal plate mounted in an insulating material. A preferred form of coupon includes a steel plate mounted in plastic.

Measurement of external corrosion conditions in the annulus of the well bore is highly desirable since such corrosion conditions may be extremely different than the corrosion conditions internally of the drill string. The present invention also enables monitoring of external corrosion at or near the same well depth as internal corrosion is being measured. It also enables measurement of the efficiency of corrosion inhibitors externally of the drill string. Mounting the corrosion coupon in an insulating material eliminates normal corrosive processes that occur with wet metal to metal contact (e.g., galvanic, localized cell, pH, and potential differentials).

BRIEF DESCRIPTION OF THE DRAWINGS

The invention is described in more detail hereinafter with reference to the accompanying drawings wherein like reference characters refer to the same parts throughout the several views and in which:

FIG. 4 shows the annular corrosion sub in a drill string in a well bore; and

DETAILED DESCRIPTION OF THE INVENTION

Figure 2:
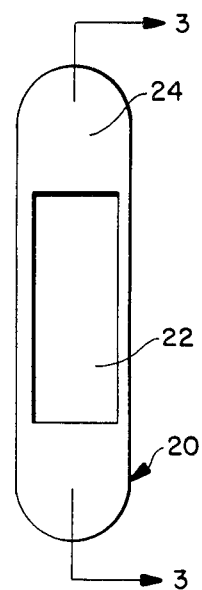
FIG. 2 is a top view of a test coupon of this invention.
Figure 1:
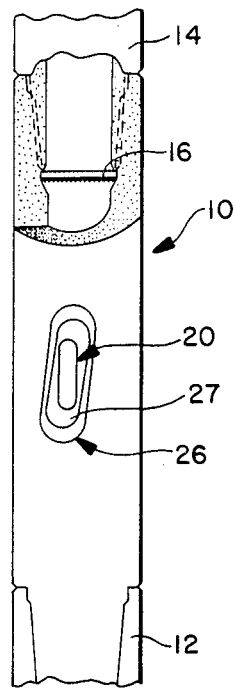
FIG. 1 is a partial cut-away elevational view of an annular corrosion sub of the present invention.
Figure 3:
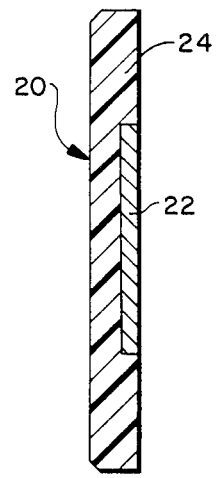
FIG. 3 is a cross-section view of the test coupon shown in FIG. 2.

Thus, in FIG. 1 there is shown a portion of a drill string which includes drill string segments 12 and 14. Fastened between these segments is an annular corrosion sub 10 of the present invention. Sub 10 is threadably connected at each end to the segments of the drill string. The sub is cylindrical and is usually and preferably connected in the drill string about 30 to 180 feet above the top drill collar.

The bottom or lower end of the drill string (i.e., about the lower 800 feet) includes a number of drill collars (so-called heavy joints) which provide desirable weight to keep the drill pipe in tension. The number and size of drill collars used depends upon the amount of weight desired. The drill string may or may not include a drilling bit (i.e., the lower end of the drill string may be open ended or may include a coring tool).

Annular corrosion sub 10 preferably has a diameter which is the same as the diameter of the two segments it is connected between in the drill string. For example, a common outside diameter would about 6.25 inches and the inside diameter would be about 2.25–2.5 inches. The length of the sub may vary, depending upon user preferences. For example, it may be as short as 2 feet or it may be as long as a typical drill collar (i.e., 31 feet). A typical preferred length is about three feet. The normal length of a single segment of drill pipe is 30 feet. Well depths may reach 30,000 feet.

As shown in the drawings, the sub 10 has a longitudinal bore therethrough. FIGS. 1 and 4 show the preferred manner in which a circular internal corrosion test ring 16 is retained between one end of the sub and the abutting end of one of the drill pipe segments 14. The internal test ring 16 preferably comprises a metal ring shaped portion 17 contained within an insulating material 18 such as plastic, although internal corrosion rings consisting only of steel are also useful. The circular internal test ring has been used previously to measure corrosion of the interior of the drill pipe.

As shown in FIG. 4, one end of the sub 10 includes female threading which is adapted to threadably engage an abutting end of drill pipe segment 14. The circular internal corrosion test ring 16 is adapted to be retained securely in the recessed area below the threaded portion of the sub end. As the male threaded end of drill segment 14 is turned into the female end of the sub, the lower end of segment 14 is urged against one side of the internal test ring 16 and thereby firmly and securely retains the test ring in the desired position.

Standard connections between the sub and drill string segments are not machined in a manner which provides for firm securement of a circular internal corrosion test ring. Rather, the standard connections provide too much space for the test ring. Consequently, there may be excessive wear of the test rings in such standard connections during use. In the present invention the female end of the sub is machined in such a manner that the test ring is firmly and securely retained in the desired position by the inner end of the abutting drill segment. This decreases mechanical wear of the internal test ring. The firm securement of the test ring also avoids interference with wire line testing tools passed down through the internal bore of the drill string.

To the exterior of the sub there is attached at least one test coupon 20 which comprises metal plate 22 mounted in an insulating material 24 in such a manner that a portion of the plate is adapted to be exposed to fluids in the well bore 11 externally of the sub. The formation through which the well bore extends is denoted as 9. The test coupon 20 is adapted to monitor corrosion of the exterior surface of the drill string.

The sub 10 is a short section of drill stem which preferably meets American Petroleum Institute Specification No. 7, incorporated herein by reference. The sub is adapted to be threadably connected at each end to the drill pipe segments.

Preferably the test coupon 20 is attached to the exterior of the sub within a cavity or recess 26. The lower level of the recess is slightly larger than the test coupon 20 so that it will readily receive the test coupon therein in such a manner that the top surface of the coupon does not project above the upper level of the recess in the sub, as shown in FIG. 4. The walls 27 of the recess are preferably sloped or bevelled at an angle in the range of about 15°–60° (more preferably 30°).

Preferably the top surface of the coupon is slightly below the major outer surface of the sub, whereby a portion of the walls of the recess are exposed above the test coupon. The orientation of the upper level of the recess is such that it is angled approximately 1°–20° from the longitudinal direction of the sub, as shown in FIG. 1, to allow for laminar fluid flow across the surface of the test coupon in the well bore. The preferred angle is about 5°–15°. The test coupon may be longitudinally aligned (as shown in FIG. 1) or it may be angled slightly (e.g., about 1°–10°) in a clockwise direction.

The design and orientation of the recess are such that the test coupon is protected from mechanical wear during use, yet it maximizes exposure of the coupon to the drilling fluid and does not deleteriously affect the structural strength of the sub.

Drilling fluid is typically pumped downwardly through the internal bore in the drill string and fluids are accordingly forced upwardly in the well bore externally of the drill string. This is represented by the arrows in FIG. 4. The direction of rotation of the drill string in the well bore is clockwise.

The test coupon preferably comprises a metal plate (such as AISI 4130 or API grade steel) which is rectangular and includes a flat planar surface which is adapted to be exposed to the fluids external of the sub in the well bore. The metal plate is mounted in an insulating material such as plastic.

The metal plate typically has a thickness in the range of about 0.05 to about 0.5 inch, a width in the range of about 0.25 to about 1.5 inch, and a length in the range of about 0.5 to about 6 inches. A preferred size is about 0.125 inch by 1 inch by 2 inches.

Figure 5:
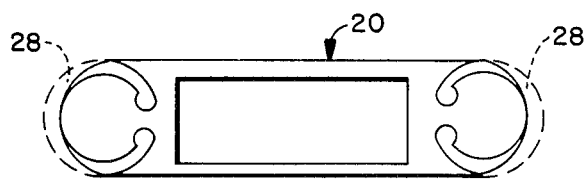
FIG. 5 shows one manner in which the test coupon may be retained on the sub.

The test coupon may be attached to the sub in a variety of manners. A preferred manner of detachably fastening the coupon to the sub is by means of spring clips 28 which are adapted to engage horizontal slots in the sub just above the position of the test coupon in the recess 26. This is illustrated in FIG. 5, for example.

Positioning of the external test coupon in a recess avoids unnecessary and undesirable contact with the sides of the well bore. Accordingly, mechanical wear and damage to the test coupon is minimized. This also prevents the test coupon from being dislodged during use.

Each coupon (i.e., both the internal test ring and external test coupon) is weighed before it is attached to the drill string. After a period of time in the well bore each coupon may be removed and weighed again to determine the rate of corrosion. If desired, of course, more than one external test coupon may be included in a drill string.

Alternatively, the thickness of the test coupon may be measured after it has been in the well bore (attached to the drill string in accordance with the techniques of this invention). The resulting thickness of the test coupon (and the depth and types of pits therein) provide indication of the type and extent of the corrosion taking place. The measurements may be made with appropriate micrometers or they may be made with a sonic probe, for example.

Other variants are possible without departing from the scope of the present invention.

What is claimed is:

1. A method for measuring corrosion in a well bore during drilling, said method comprising the steps of:
    (a) providing a drill string;
    (b) positioning an internal corrosion test ring within said drill string in a manner such that said test ring is exposed to internal fluids within said string;
    (c) positioning a corrosion test coupon on the external surface of said drill string in such a manner that said test coupon is exposed to fluids within said well bore externally of said drill string;
    (d) measuring the amount of corrosion of said test ring and said test coupon after operating said drilling string in said well bore.

2. A method in accordance with claim 1, wherein said test coupon comprises a metal plate mounted in an insulating material.

3. A method in accordance with claim 2, wherein said metal plate comprises a layer of steel and said insulating material comprises plastic, and wherein one major surface of said layer is exposed to said fluids externally of said drill string.

4. A method in accordance with claim 3, wherein said layer has a length in the range of about 0.5 to 6 inches and a width in the range of about 0.25 to 1.5 inch.

5. A method in accordance with claim 1, wherein said test coupon is attached to a sub connected between adjacent segments of said drill string.

6. A method in accordance with claim 5, wherein said test coupon is retained in a recess in said sub.

7. A method in accordance with claim 6, wherein said recess is elongated and wherein said test coupon is retained in said recess in a manner such that a portion of the walls of said recess is exposed above said test coupon.

8. A method in accordance with claim 7, wherein said walls of said recess are sloped.

9. A method in accordance with claim 7, wherein the top portion of said recess is angled approximately 1° to 20° from the longitudinal axis of said sub.

10. A method in accordance with claim 5, wherein said internal corrosion test ring is retained between one end of said sub and one of said segments of said drill string.

* * * * *